United States Patent [19]

Miller et al.

[11] Patent Number: 5,681,473

[45] Date of Patent: Oct. 28, 1997

[54] MEMBRANE SEPARATION PROCESS

[75] Inventors: Jay Fingeret Miller, Charleston; David Robert Bryant, South Charleston; Kenneth Look Hoy, Saint Albans; Nancy Ellen Kinkade, Charleston, all of W. Va.; Rachel Hilda Zanapalidou, Winchester, Mass.

[73] Assignee: Union Carbide Chemicals & Plastics Technology Corporation, Danbury, Conn.

[21] Appl. No.: 430,790

[22] Filed: May 5, 1995

Related U.S. Application Data

[63] Continuation-in-part of Ser. No. 432,092, May 1, 1995, abandoned.

[51] Int. Cl.$^6$ ............................................. B01D 61/00
[52] U.S. Cl. ........................ 210/651; 210/651; 210/640; 210/653
[58] Field of Search .......................... 210/651, 652, 210/653, 654, 640; 568/429, 426, 427

[56] References Cited

U.S. PATENT DOCUMENTS

| | | | |
|---|---|---|---|
| 3,420,898 | 1/1969 | Van Winkle et al. | 260/632 |
| 3,440,291 | 4/1969 | Van Winkle et al. | 260/632 |
| 3,496,203 | 2/1970 | Morris et al. | 260/439 |
| 3,496,204 | 2/1970 | Morris et al. | 260/439 |
| 3,501,515 | 3/1970 | Van Winkle et al. | 260/439 |
| 3,617,553 | 11/1971 | Westaway et al. | |
| 4,252,652 | 2/1981 | Elfert et al. | 210/654 |
| 4,363,765 | 12/1982 | Fiato et al. | 260/429 R |
| 4,717,775 | 1/1988 | Billig et al. | 568/454 |
| 4,769,498 | 9/1988 | Billig et al. | 568/454 |
| 4,774,361 | 9/1988 | Maher et al. | 568/454 |
| 4,885,401 | 12/1989 | Billig et al. | 568/454 |
| 5,113,022 | 5/1992 | Abatjoglu et al. | 568/454 |
| 5,143,620 | 9/1992 | Chou et al. | 210/640 |
| 5,174,899 | 12/1992 | Bahrmann et al. | 210/644 |
| 5,205,934 | 4/1993 | Linder et al. | 210/500.43 |
| 5,215,667 | 6/1993 | Livingston et al. | 210/651 |
| 5,264,616 | 11/1993 | Roeper et al. | 560/175 |
| 5,265,734 | 11/1993 | Linder et al. | 210/654 |
| 5,288,818 | 2/1994 | Livingston et al. | 210/640 |
| 5,288,918 | 2/1994 | Maher et al. | 568/454 |
| 5,298,699 | 3/1994 | Healy et al. | 568/492 |
| 5,312,996 | 5/1994 | Packett | 568/454 |
| 5,360,938 | 11/1994 | Babin et al. | 568/449 |
| 5,364,950 | 11/1994 | Babin et al. | 556/2 |
| 5,395,979 | 3/1995 | Deckman et al. | 568/454 |
| 5,430,194 | 7/1995 | Barner et al. | 568/429 |

FOREIGN PATENT DOCUMENTS

| | | |
|---|---|---|
| 263953 | 4/1988 | European Pat. Off. . |
| 0532199 | 3/1993 | European Pat. Off. . |
| 2021810 | 7/1970 | France . |
| 3245318 | 6/1984 | Germany . |
| 8700881 | 11/1988 | Netherlands . |
| 988941 | 4/1965 | United Kingdom . |
| 1109787 | 4/1968 | United Kingdom . |
| 1243507 | 8/1971 | United Kingdom . |
| 1243508 | 8/1971 | United Kingdom . |
| 1260733 | 1/1972 | United Kingdom . |
| 1266180 | 3/1972 | United Kingdom . |
| 1312076 | 4/1973 | United Kingdom . |
| 1432561 | 4/1976 | United Kingdom . |
| WO9419104 | 9/1994 | WIPO . |
| WO9600200 | 1/1996 | WIPO . |

*Primary Examiner*—Ana Fortuna
*Attorney, Agent, or Firm*—G. L. Coon

[57] ABSTRACT

This invention relates to membrane separation of organic solubilized rhodium-organophosphite complex catalyst and free organophosphite ligand from a homogeneous non-aqueous hydroformylation reaction mixture, said mixture also containing, in addition to said catalyst and free ligand, aldehyde product and an organic solvent.

11 Claims, No Drawings

MEMBRANE SEPARATION PROCESS

RELATED APPLICATION

This application is a continuation-in-part of U.S. application Ser. No. 08/432,092 entitled MEMRANE SEPARATION, filed May 1, 1995 now abandoned.

BRIEF SUMMARY OF THE INVENTION

1. Technical Field

This invention relates to membrane separation of organic solubilized rhodium-organophosphite complex catalyst and free organophosphite ligand from a homogeneous non-aqueous hydroformylation reaction mixture, said mixture also containing, in addition to said catalyst and free ligand, aldehyde product and an organic solvent.

2. Background of the Invention

Methods for producing aldehyde products by asymmetric or non-asymmetric hydroformylation of an olefin with carbon monoxide and hydrogen (more commonly referred to as synthesis gas or syn gas) in the presence of a rhodium-organophosphite complex catalyst and free phosphite ligand are well known in the art as seen e.g. by U.S. Pat. Nos. 4,599,206; 4,668,651; 4,717,775; 4,737,588; 4,748,261; 4,769,498; 4,774,361; 4,789,753; 4,885,401; 5,059,710; 5,113,022; 5,288,918; 5,312,996; 5,360,938 and 5,364,950.

Such non-asymmetric hydroformylation processes are preferably directed to producing aldehyde product mixtures of widely varying normal (straight chain) to isomer (branched chain) aldehyde product ratios, while such asymmetric hydroformylation process are preferably directed to forming enantiomeric aldehyde products, i.e. optically active aldehydes. Moreover, both types of such hydroformylation processes are carried out in a non-aqueous hydroformylation reaction medium. In such processes the desired aldehyde product is preferably separated and recovered from the reaction product medium by distillation, and in liquid catalyst recycle operations, the non-volatilized catalyst-ligand containing residue is returned to the reactor.

Accordingly, effective separation and recovery of the desired aldehyde product from its hydroformylation reaction product medium without excessive loss of the free organophosphite ligand and rhodium organophosphite complex catalyst is very important.

When low molecular weight olefins are hydroformylated in non-aqueous systems, aldehyde product separation while a concern, is generally not an overwhelming problem. However, this problem is increased and magnified when the process is directed to the hydroformylation of longer chain olefinic compounds for producing the corresponding higher molecular weight aldehydes. Higher temperatures and harsher conditions necessary to volatilize the higher molecular weight aldehyde products during separation from the hydroformylation reaction product medium may eventually lead to excessive loss (via chemical and thermal degradation) of even the phosphite ligands, particularly over the normally prolonged periods of reaction time required for a successful commercial operation.

A similar problem is presented when higher boiling aldehyde condensation by-products, such as trimers and tetramers are formed during hydroformylation and are desired to be separated from catalyst-containing hydroformylation recycle residues after separate recovery of the hydroformylation aldehyde product.

Thus, the discovery of a simpler, more gentle, separation procedure that would allow for excellent removal of the organic solubilized rhodium-organophosphite complex catalyst and free organophosphite ligand from higher molecular weight aldehyde product containing hydroformylation reaction mixtures, while avoiding such problems attendant with distillation separation, would obviously be highly beneficial to the art, and it is believed that such a discovery is provided by the subject invention which relates to the use of membrane separation.

Now the use of the various membrane systems to separate various liquids from solutes contained therein are known. Such processes comprise bringing a solution which contains at least one solute in at least one solvent into intimate contact with a semi-permeable membrane, which allows the solvent and other primary liquids to pass through, while rejecting the solute. The solution which passes through the membrane is termed the permeate, and the solution (solute) that does not pass through (i.e. that is rejected by) the membrane is termed the raffinate. The feed solution is typically at a pressure greater than the osmotic pressure difference between the osmotic pressure of the raffinate and that of the permeate.

By way of example, U.S. Pat. Nos. 5,215,667; 5,288,818; 5,298,669; are all directed to the use of a hydrophobic membrane to separate water-soluble Group VIII noble metal ionic phosphine ligand complex catalysts from aldehyde containing hydroformylation reaction mediums comprising aqueous solutions, emulsions or suspensions of said catalysts. The subject invention does not involve such aqueous systems or phosphine ligands.

PCT International Publication No. WO 94/19104 is directed to separating a homogeneous hydrocarbon soluble rhodium-alkylated or arylated phosphine complex catalyst from a crude aldehyde containing hydroformylation reaction product via a membrane separation procedure. The subject invention is not directed to the use of such rhodium-phosphine complex type catalysts or ligands.

It has been proposed in a series of British patents to separate transition metal complexes, e.g. rhodium-trialkylphosphine complex hydroformylation catalysts, from a solution in an organic solvent component e.g. alcohols, aldehydes, ketones, organic acids, phosphines and amides by a process which comprises bringing the solution into contact with one side of a cellulosic membrane (B.P. 1,243,507 which corresponds to U.S. Pat. No. 3,617,553), or a silicone rubber membrane (B.P. 1,243,508) or a polyolefin membrane (B.P. 1,260,733) or a polyamide membrane (B.P. 1,266,180) at an applied pressure greater than the pressure on the opposite side of the membrane, the pressure differential being greater than the osmotic pressure of the system. Likewise, British Patent 1,312,076 proposes to use the same membranes and separation process of said four previously mentioned British Patents to separate hydroformylation transition metal catalysts from a liquid side stream of the high boiling by-products of the hydroformylation process after removal of the aldehyde product via distillation. According to this patent aldehydes produced during the hydroformylation process are continuously withdrawn from the reactor as an overhead vapor product stream, while a liquid stream comprising the complex catalyst, aldehyde and high boiling residues are passed under reaction pressure over the surface of a membrane wherein the catalyst is retained and recycled to the reactor, while a portion of the high boiling residues and aldehydes permeates through the membrane and is removed. The transition metal catalysts are preferably rhodium beta-diketonate complexes which may contain or be free of other ligands such as trialkylphosphines. The subject invention does not involve such rhodium-phosphine complex type catalyst or rhodium complex catalysts free of organophosphite ligands.

In like manner British Patent 1,432,561 proposes a process for the hydroformylation of olefins which comprises reacting an olefin at elevated temperature and pressure with carbon monoxide and hydrogen in the presence of a catalyst complex of a Group VIII metal (e.g. cobalt or rhodium) and a biphyllic ligand of trivalent phosphorus, arsenic or antimony (e.g. the catalyst of B.P. 988,941 and 1,109,787) to give a crude liquid hydroformylation product containing an aldehyde and/or alcohol, separating aldehyde and/or alcohol from the crude product and leaving a liquid, and bringing the liquid optionally after separation of the Group VIII metal compound and substantially free from aldehyde and alcohol, under reverse osmosis conditions into contact with one side of a silicone rubber semi-permeable membrane in which the polymer chains have been at least partly cross-linked by gamma-radiation, whereby the liquid retained by the membrane contains a higher concentration of the Group VIII metal compound and/or biphyllic ligand than the original liquid. The preferred Group VIII metal compounds are cobalt compounds. The reference does not specifically disclose removal of the rhodium-organophosphite complex catalysts and free organophosphite ligands of the subject invention.

Dutch Patent No. 8700881 proposes an improved membrane process for separating Group VIII metal hydroformylation catalysts (e.g. cobalt or rhodium-organophosphine complexes) and free phosphine ligand from their crude aldehyde product containing hydroformylation mixtures which comprises employing membranes of silicone rubber or modified derivatives there of in combination with an aromatic deswelling agent such as nonpolar hydrocarbons which contain no oxygen or halogen, such as alkanes with 5–35 carbon atoms and aromatic compounds with 6–25 carbon atoms. The subject invention does not involve such cobalt or rhodium-phosphine complex type catalysts or ligands.

U.S. Pat. No. 5,174,899 discloses that semi-permeable membranes of aromatic polyamides can be used to separate metal complex catalysts from organic solvents, e.g. rhodium-triphenylphosphine or phosphane and ammonium salts of sulfonated or carboxylated triarylphosphanes from hydroformylation aldehyde product mixtures. The subject invention does not involve such rhodium-phosphine or phosphane complex type catalysts.

U.S. Pat. No. 5,265,734 is directed to employing composite membranes of crosslinked silicone (e.g. polysiloxanes) on a substrate for concentrating and purifying (i.e., separating) organic solutes, such as dyes, dye intermediates, optical brightners, antibiotics, peptides, proteins, enzymes, hormones, and herbicides in organic solvents or in aqueous/organic mixtures, as well as other liquid streams such as lubricating oils in strong organic solvents, catalysts dissolved in organic solvents, e.g. metal organic complexes useful for performing catalytically enhanced polymerization reactions in organic media, and low molecular weight oligomers in paint wastes dissolved in strong organic solvents. The reference does not specifically disclose removal of the rhodium-organophosphite complex catalysts and free organophosphite ligands oft he subject invention.

DISCLOSURE OF THE INVENTION

It has now been discovered that certain composite membranes may be employed to effectively separate organic solubilized rhodium-organophosphite complex catalyst and free organophosphite ligand from a homogeneous non-aqueous hydroformylation reaction mixture, said mixture also containing, in addition to said catalyst and free ligand, aldehyde product, and an organic solvent.

Thus it is an object of this invention to provide a process for separating organic solubilized rhodium-organophosphite complex catalyst and free organophosphite ligand from a homogeneous non-aqueous hydroformylation reaction mixture. Other objects and advantages of this invention will become readily apparent from the following written description and appended claims.

Accordingly, a generic aspect of this invention can be described as a process for separating an organic solubilized rhodium-organophosphite complex catalyst and free organophosphite ligand from a non-aqueous hydroformylation reaction mixture, said mixture containing, in addition to said catalyst and free ligand, aldehyde product and an organic solvent, which comprises, (i) contacting said non-aqueous hydroformylation reaction mixture with a composite membrane so as to allow a substantial portion of said aldehyde product and organic solvent to pass through said membrane, while rejecting at least 90 percent by weight of said catalyst and free ligand; wherein said aldehyde product has a solubility parameter in relation to the solubility parameter of the membrane of said composite membrane of at least $\pm 50$ $\sqrt{kJ/m^3}$ units, but not more than $\pm 500$ $\sqrt{kJ/m^3}$ units, and wherein the ratio of the molar volume of said organophosphite ligand to said aldehyde product is $\geq 1.5$; and (ii) recovering said aldehyde product and organic solvent as a permeate.

DETAILED DESCRIPTION

As noted above the subject invention generically encompasses separating organic solubilized rhodium-organophosphite complex catalyst and free organophosphite ligand from homogeneous non-aqueous hydroformylation reaction mixture, or any part thereof, containing in addition to said catalyst and free ligand, aldehyde product and an organic solvent.

Thus the homogeneous non-aqueous hydroformylation reaction mixture starting materials of this invention may be provided by any suitable known asymmetric or non-asymmetric hydroformylation process directed to producing aldehydes from olefins. Moreover, as indicated above, methods for hydroformylating olefinic compounds to produce aldehydes using a reaction medium comprising an organic solution containing a solubilized rhodium-organophosphite ligand complex catalyst, free organophosphite ligand, and an organic solvent are well known in the art. Thus it should be clear that the particular hydroformylation process for producing such aldehydes from an olefinic compound, as well as the reaction conditions and ingredients of the hydroformylation process, which serve only as a means for furnishing the organic solution starting material of the present invention, are not critical features of the present invention. Accordingly it should be sufficient for the purpose of this invention to understand that whatever compounds are present during the hydroformylation process from which the organic solution starting materials of this invention are derived, may also be correspondingly present in the organic solution starting materials of this invention.

In general, such hydroformylation reactions involve the production of aldehydes by reacting an olefinic compound with carbon monoxide and hydrogen in the presence of a solubilized rhodium-organophosphite complex catalyst and free organophosphite ligand in a liquid medium that also contains a solvent for the catalyst and ligand. The process may be carried out in a continuous single pass mode or more preferably in a continuous liquid catalyst recycle manner. The recycle procedure generally involves withdrawing a portion of the liquid reaction medium containing the catalyst, ligand and aldehyde product from the hydroformylation reaction zone, either continuously or intermittently, and removing the aldehyde product therefrom as appropriate, the rhodium catalyst containing residue being recycled to the reaction zone. The aldehyde product can be passed on for further purification if desired and any recovered reactants, e.g., olefinic starting material and syn gas recycled in any desired manner to the hydroformylation zone. Likewise, the recovered rhodium catalyst containing residue can be recycled to the hydroformylation zone in any conventional manner desired. Accordingly, the hydroformylation processing techniques of this invention may correspond to any known processing techniques such as preferably employed in conventional liquid catalyst recycle hydroformylation reactions.

Accordingly the non-aqueous hydroformylation reaction mixture starting materials employable herein includes any organic solution derived from any corresponding hydroformylation process that contains at least some amount of four different main ingredients or components, i.e., the aldehyde product, a rhodium-organophosphite ligand complex catalyst, free organophosphite ligand and an organic solubilizing agent for said catalyst and said free ligand, said ingredients corresponding to those employed and/or produced by the non-aqueous hydroformylation process from whence the non-aqueous hydroformylation reaction mixture starting material may be derived. Of course it is to be further understood that the non-aqueous hydroformylation reaction mixture compositions employable herein can and normally will contain minor amounts of additional ingredients such as those which have either been deliberately employed in the non-aqueous hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation by-products, as well as other inert co-solvent type materials or hydrocarbon additives, if employed. Preferably however the hydroformylation reaction mixture starting materials of this invention are free of any deliberately added additive whose primary purpose is to act as a deswelling agent for the composite membrane employed in the particular process involved.

As noted, the non-aqueous hydroformylation reaction mixtures employable herein contain both a rhodium-organophosphite ligand complex catalyst and free organophosphite ligand. By "free ligand" is meant organophosphite ligand that is not complexed with (tied to or bound to) the rhodium atom of the complex catalyst. Moreover the term "non-aqueous" as employed herein with regard to the hydroformylation process from whence the non-aqueous hydroformylation reaction mixture starting materials of this invention may be derived means that the hydroformylation reaction is conducted, in the absence or essential absence of water, which is to say that any water, if present at all, in the hydroformylation reaction medium, is not present in an amount sufficient to cause either the hydroformylation reaction or said medium to be considered as encompassing a separate aqueous or water phase or layer in addition to an organic phase. Similarly, the term "non-aqueous" as employed herein with regard to the hydroformylation reaction mixture starting materials of this invention means that said reaction mixture starting materials are also free or essentially free of water, which is to say that any water, if present at all in said hydroformylation reaction mixture starting materials is not present in an amount sufficient to cause the hydroformylation reaction mixture starting material to be considered as encompassing a separate aqueous or water phase or layer in addition to an organic phase.

Among the organophosphites that may serve as the ligand of the rhodium-organophosphite complex catalyst and/or free ligand of the hydroformylation reaction mixture starting materials of this invention are monoorganophosphite, diorganophosphite, and organopolyphosphites that are well known in the art.

Representative diorganophosphites may include those having the formula:

wherein, $R^1$ represents a divalent organic radical containing from 4 to 40 carbon atoms and W represents a substituted or unsubstituted monovalent hydrocarbon radical containing from 1 to 18 carbon atoms.

Representative monovalent hydrocarbon radicals represented by W in the above formula include alkyl and aryl radicals, while representative divalent organic radicals represented by $R^1$ include divalent acyclic radicals and divalent aromatic radicals. Illustrative divalent acyclic radicals are e.g., alkylene, alkylene-oxyalkylene, alkylene-NX-alkylene wherein X is hydrogen or a monovalent hydrocarbon radical, alkylene-S-alkylene, and cycloalkylene radicals, and the like. The more preferred acyclic radicals are the divalent alkylene radicals such as disclosed more fully e.g., in U.S. Pat. Nos. 3,415,906 and 4,567,302 and the like, the entire disclosures of which are incorporated herein by reference thereto. Illustrative divalent aromatic radicals are e.g., arylene, bisarylene, arylene-alkylene, arylene-alkylene-arylene, arylene-oxy-arylene, arylene-NX-arylene wherein X is hydrogen or a monovalent hydrocarbon radical, arylene-S-arylene, and arylene-S-alkylene, and the like. More preferably $R^1$ is a divalent aromatic radical such as disclosed more fully e.g., in U.S. Pat. Nos. 4,599,206 and 4,717,775, and the like, the entire disclosures of which are incorporated herein by reference thereto.

Representative organopolyphosphites contain two or more tertiary (trivalent) phosphorus atoms and may include those having the formula:

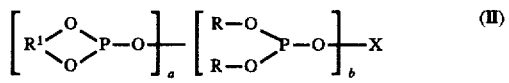

wherein X represents a substituted or unsubstituted m valent hydrocarbon radical containing from 2 to 40 carbon atoms, wherein $R^1$ is the same as defined in Formula I above, wherein each R radical is independently a substituted or unsubstituted monovalent hydrocarbon radical containing from 1 to 18 carbon atoms, wherein a and b can each have a value of 0 to 6, with the proviso that the sum of a+b is 2 to 6 and m equals a+b. Of course it is to be understood that when a has a value of 2 or more, each $R^1$ radical may be the same or different Illustrative preferred organopolyphosphites may include bisphosphites such as those of formulas III to V below:

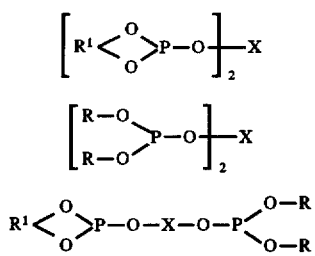

(III)

(IV)

(V)

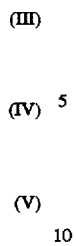

wherein each R, R¹ and X of Formulas III to V are the same as defined above for Formula II. Preferably each R, R¹ and X represents a divalent hydrocarbon radical selected from the group consisting of alkylene, alkylene-oxy-alkylene, arylene and bisarylene, while each R radical represents a monovalent hydrocarbon radical selected from the group consisting of alkyl and aryl radicals. Such phosphites of Formulas (II) to (V) may be found described in greater detail in U.S. Pat. Nos. 4,769,498; 4,885,401; 5,364,950 and 5,264,616, the entire disclosures of which are incorporated herein by reference thereto.

Representative mono-organophosphites may include those having the formula:

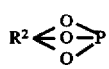

(VI)

wherein $R^2$ represents a trivalent organic radical containing from 6 to 18 carbon atoms, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such mono-organophosphites may be found described in greater detail e.g., in U.S. Pat. No. 4,567,306, the entire disclosure of which is incorporated herein by reference thereto.

Representative of a more preferred class of diorganophosphites are those of the formula:

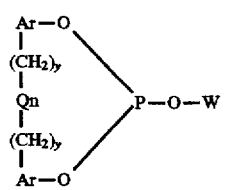

(VII)

wherein W represents a substituted or unsubstituted monovalent hydrocarbon radical as defined above, wherein each Ar radical individually represents a substituted or unsubstituted aryl radical, wherein each y has a value of 0 or 1, wherein Q represents a divalent bridging group selected from the group consisting of $-CR^3R^4-$, $-O-$, $-S-$, $-NR^5-$, $SiR^6R^7-$ and $-CO-$, wherein each $R^3$ and $R^4$ independently represents a radical selected from the group consisting of hydrogen, alkyl radicals having from 1 to 12 carbon atoms, phenyl, tolyl, and anisyl, wherein each $R^5$, $R^6$ and $R^7$ independently represent hydrogen or a methyl radical, and n has a value of 0 or 1. Such diorganophosphites are described in greater detail e.g., in U.S. Pat. Nos. 4,599,206 and 4,717,775, the entire disclosures of which are incorporated herein by reference thereto.

Representative of more preferred classes of organobisphosphites are those of the following Formulas VIII to X

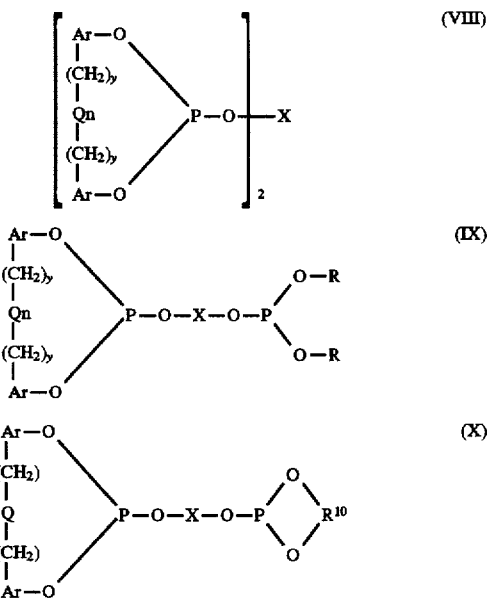

wherein Ar, Q, R, X, n, and y are the same as defined above and $R^{10}$ represents a divalent hydrocarbon radical selected from the group consisting of alkylene, alkylene-oxy-alkylene and arylene radicals. See e.g., U.S. Pat. Nos. 4,769,498; 4,885,401; 5,364,950 and 5,264,616. Most preferably X represents a divalent aryl—$(CH_2)_y$—$(Q)_n$—$(CH_2)_y$—aryl radical wherein each y individually has a value of 0 or 1; wherein n has a value of 0 or 1 and wherein Q is —$CR^3R^4$— where R3 and R4 individually represent a hydrogen or methyl radical. More preferably each aryl radical of the above-defined Ar, X, R, $R^1$, $R^{10}$ and W groups of the above formulae may contain from 6 to 18 carbon atoms and may be the same or different while preferred arkylene radicals X may contain from 2 to 18 carbon atoms and the preferred alkylene radicals of $R^{10}$ may contain from 5 to 18 carbon atoms. In addition, preferably the divalent Ar radicals and divalent aryl radicals of X of the above formulae are phenylene radicals in which the bridging group represented by —$(CH_2)_y$—$(Q)_n$—$(CH_2)_y$— is bonded to said phenylene radicals in positions that are ortho to the oxygen atoms of the formulae that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above Formulas I to X may be an ionic phosphite, i.e., may contain one or more ionic moieties selected from the group consisting of:

$SO_3M$ wherein M represents inorganic or organic cationic atoms or radicals, $PO_3M$ wherein M represents inorganic or organic cationic atoms or radicals, $NR_3X'$ wherein each R represents a hydrocarbon radical containing from 1 to 30 carbon atoms selected from the class consisting of alkyl, aryl, alkaryl, aralkyl, and cycloalkyl radicals, and X' represents inorganic or organic anionic atoms or radicals, $CO_2M$ wherein M represents inorganic or organic cationic atoms or radicals, as described e.g., in U.S. Pat. Nos. 5,059,710; 5,113,022 and 5,114,473 the entire disclosures of which are incorporated herein by reference thereto. Thus if desired such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and X', for the anionic moieties of the ionic phosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation and quaternary ammonium cations. Suitable anionic atoms of radicals include, for example, sulfate, carbonate, phosphate, chloride, acetate, oxalate and the like.

Of course any of the R, $R^1$, $R^2$, $R^{10}$, W, X and Ar radicals of such non-ionic and ionic organophosphites of Formulas I to VI above may be substituted if desired, with any suitable substituent containing from 1 to 30 carbon atoms that does not unduly adversely affect the desired result of the process or this invention. Substituents that may be on said radicals in addition of course to corresponding hydrocarbon radicals such as alkyl, aryl, aralkyl, alkaryl and cyclohexyl substituents, may include for example silyl radicals such as —Si($R^9$)$_3$; amino radicals such as —N($R^9$)$_2$; phosphine radicals such as —aryl—P($R^9$)$_2$; acyl radicals such as —C(O)$R^9$ acyloxy radicals such as —OC(O)$R^9$; amido radicals such as —CON($R^9$)$_2$ and —N($R^9$)CO$R^9$; sulfonyl radicals such as —SO$_2$$R^9$, alkoxy radicals such as —O$R^9$; thionyl radicals such as —S$R^9$, phosphonyl radicals such as —P(O)($R^9$)$_2$, as well as, halogen, nitro, cyano, trifluoromethyl, hydroxy radicals, and the like, wherein each $R^9$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N($R^9$)$_2$ each $R^9$ taken together can also represent a divalent bridging group that forms a heterocyclic radical with the nitrogen atom, and in amido substituents such as —C(O)N($R^9$)$_2$ and —N($R^9$)CO$R^9$ each $R^9$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy —OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —C$_6$H$_5$—P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; thionyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$ (C$_6$H$_5$), —P(O)(H)(C$_6$H$_5$), and the like.

Specific illustrative examples of achiral diorganophosphite and bis-phosphite ligands include, e.g.;

2-t-butyl-4-methoxyphenyl(3,3'-di-t-butyl-5,5'-dimethoxy-1,1'-biphenyl-2,2'-diyl) phosphite having the formula:

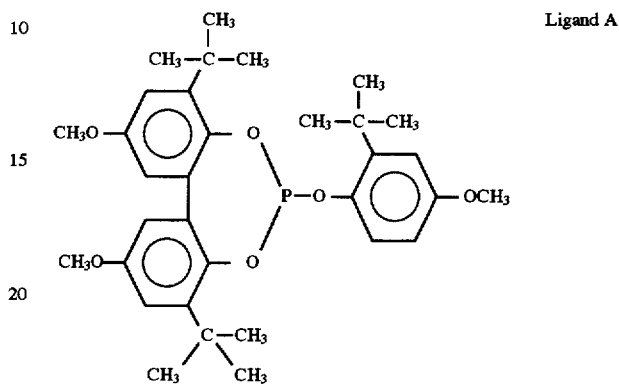

Ligand A 6,6'-[[3,3,'-bis(1,1-dimethylethyl)-5,5'-dimethoxy-[1,1'-biphenyl]-2,2'-diyl]bis(oxy)]bis-dibenzo[d,f][1,3,2]-dioxaphosphepin having the formula:

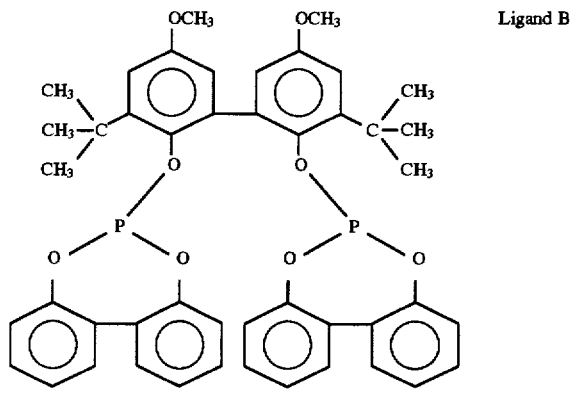

Ligand B 6,6'-[[3,3',5,5'-tetrakis(1,1-dimethylpropyl)-[1,1'-biphenyl]-2,2'-diyl]bis(oxy)]bis-dibenzo[d,f][1,3,2]-dioxaphosphepin having the formula:

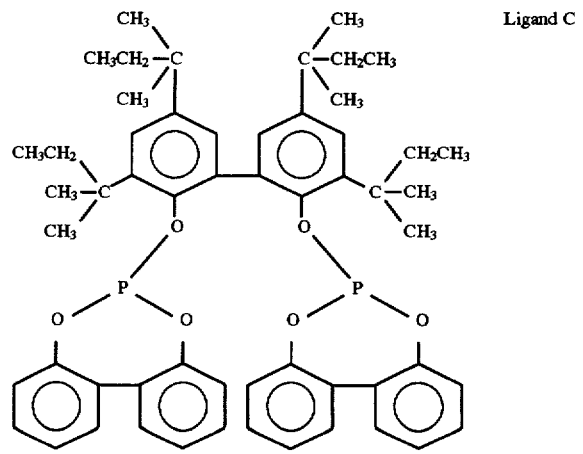

Ligand C 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula:

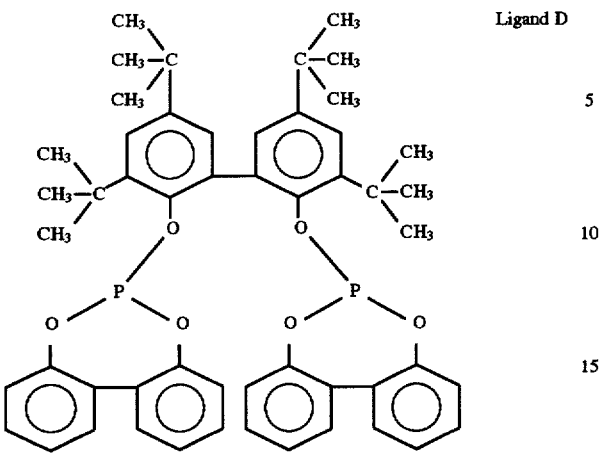
Ligand D
and the like, while specific illustrative optically active bis-phosphite ligands include, e.g.;
(2R, 4R)-Di[2,2'-(3,3',5,5'-tetrakis-tert-amyl-1,1'-biphenyl)]-2,4-pentyl diphosphite having the formula:
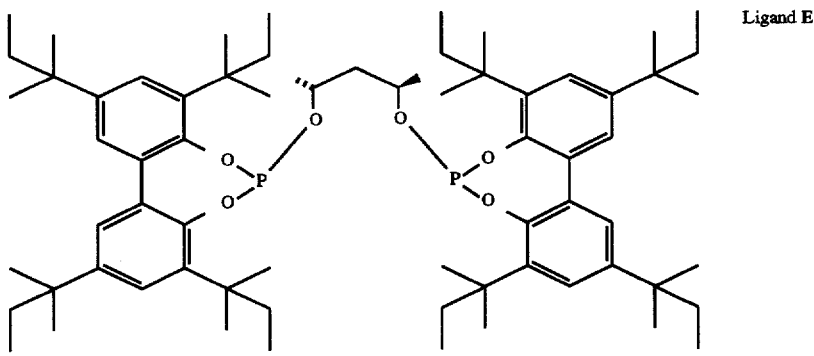
Ligand E
(2R, 4R)-Di[2,2'-(3,3',5,5'-tetrakis-tert-butyl-1,1'-biphenyl)]-2,4-pentyl diphosphite having the formula:
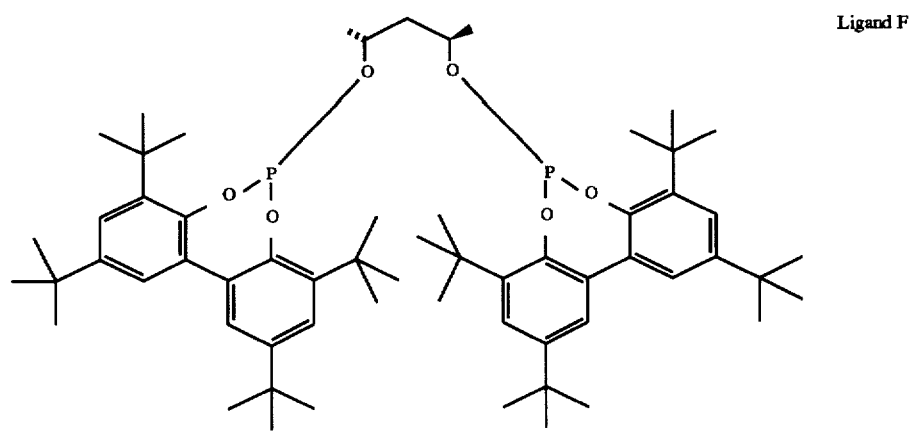
Ligand F
(2R, 4R)-Di[2,2'-(3,3'-di-amyl-5,5'-dimethoxy-1,1'-biphenyl)]-2,4-pentyl diphosphite having the formula:

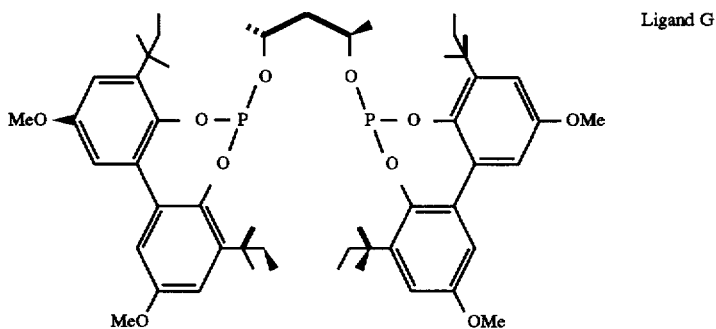
Ligand G
(2R, 4R)-Di[2,2'-(3,3'-di-tert-butyl-5,5'-dimethyl-1,1'-biphenyl)]-2,4-pentyl diphosphite formula:
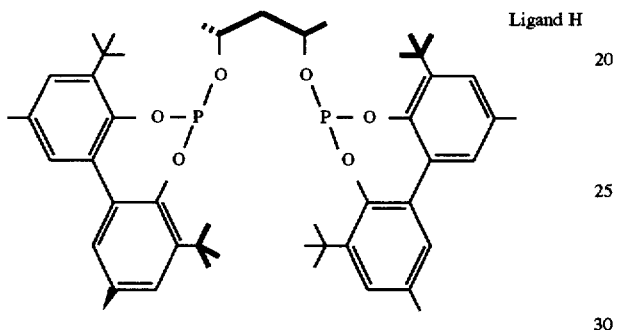
Ligand H
(2R, 4R)-Di[2,2'-(3,3'-di-tert-butyl-5,5'-diethoxy-1,1'-biphenyl)]-2,4-pentyl diphosphite having the formula:
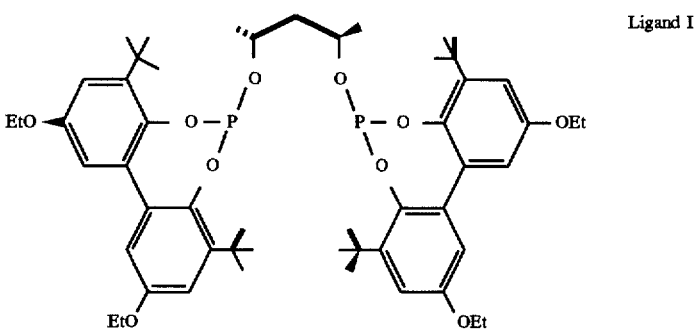
Ligand I
(2R, 4R)-Di[2,2'-(3,3'-di-tert-butyl-5,5'-diethyl-1,1'-biphenyl)]-2,4-pentyl diphosphite having the formula:
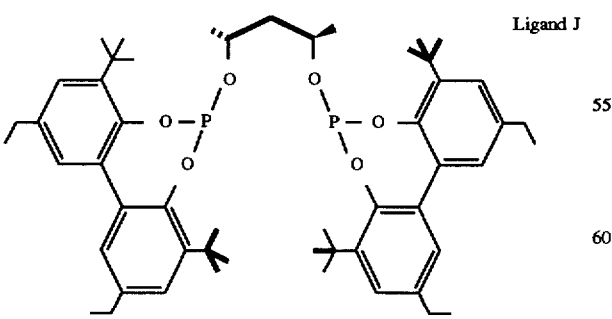
Ligand J
(2R, 4R)-Di[2,2'-(3,3'-di-tert-butyl-5,5'-dimethoxy-1,1'-biphenyl)]-2,4-pentyl diphosphite having the formula:

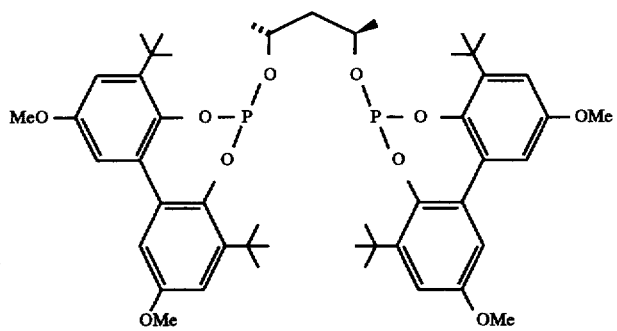

Ligand K

The phosphite ligand concentration in hydroformylation reaction mixtures used in the process of the present invention may range from between about 0.005 and 15 weight percent based on the total weight of the reaction mixture. Preferably the ligand concentration is between 0.001 and 10 weight percent, and more preferably is between about 0.05 and 5 weight percent on that basis.

The concentration of the rhodium metal in the hydroformylation reaction mixtures used in the present invention may be as high as about 2000 parts per million by weight based on the weight of the reaction mixture. Preferably the rhodium concentration is between about 50 and 1000 parts per million by weight based on the weight of the reaction mixture, and more preferably is between about 70 and 800 parts per million by weight based on the weight of the reaction mixture.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 1500 psia and more preferably less than about 500 psia. The minimum total pressure being limited predominately by the amount of reactants necessary to obtain a desired rate of reaction. More specifically the carbon monoxide partial pressure of the hydroformylation process of this invention is preferable from about 1 to about 360 psia, and more preferably from about 3 to about 270 psia, while the hydrogen partial pressure is preferably about 15 to about 480 psia and more preferably from about 30 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about $-25°$ C. to about $200°$ C. In general hydroformylation reaction temperature of about $50°$ C. to about $120°$ C. are preferred for all types of olefinic starting materials. Of course it is to be understood that when non-optically active aldehyde products are desired, achiral type olefins, catalyst and free ligands are employed and when optically active aldehyde products are desired, prochiral or chiral type olefins, catalysts and free ligands are employed. Of course, it is to be also understood that the hydroformylation reaction conditions employed will be governed by the type of aldehyde product desired.

The olefin starting material reactants that may be employed in the hydroformylation processes of this invention include both optically active (prochiral and chiral) and non-optically active (achiral) olefin compounds containing from 2 to 30, preferably 4 to 20, carbon atoms. Such olefin compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, e.g., in U.S. Pat. Nos. 4,518,809 and 4,528,403). Moreover, such olefin compounds may further contain one or more ethylenic unsaturated groups, and of course, mixtures of two or more different olefinic compounds may be employed as the starting hydroformylation material if desired. Further such olefin compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,668,651 and the like.

Illustrative achiral olefinic unsaturated compounds are alpha-olefins, internal olefins, 1,3-dienes, alkyl alkenoates, alkenyl alkanoates, alkenyl alkyl ethers, alkenols, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, butadiene, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, isosafrole, anethol, 4-allylanisole, indene, limonene, beta-pinene, dicyclopentadiene, cyclooctadiene, camphene, linalool, and the like. Illustrative preferred optically-active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

Illustrative prochiral and chiral olefins useful in the asymmetric hydroformylation that can be employed to produce enantiomeric aldehyde mixtures that may be encompassed by in this invention include those represented by the formula:

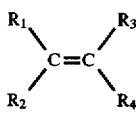

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamiuo; acylamino and diacylamino such as acetylbenzylamino and diacetylamiuo; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R-groups are connected to form ring compounds, e.g., 3-methyl-1-cyclohexene, and the like.

Mixtures of different olefinic starting materials can be employed, if desired, in the hydroformylation process of the present invention. More preferably the subject invention is especially useful for the production of achiral aldehydes, by hydroformylating alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial-alpha olefins containing four or more carbon atoms may contain minor amounts of corresponding internal olefins and/or their corresponding saturated hydrocarbon and that such commercial olefins need not necessarily be purified from same prior to being hydroformylated.

As noted the hydroformylation processes of this invention involve the use of a rhodium-organophosphite ligand complex catalyst as described herein. Of course mixtures of such catalysts can also be employed if desired. The amount of rhodium-organophosphite complex catalyst present in the reaction medium of a given hydroformylation process encompassed by this invention need only be that minimum amount necessary to provide the given rhodium concentration desired to be employed and which will furnish the basis for at least the catalytic amount of rhodium necessary to catalyze the particular hydroformylation process involved such as disclosed e.g. in the above-mentioned patents. In general, rhodium concentrations in the range of from about 10 ppm to about 1000 ppm, calculated as free rhodium, in the hydroformylation reaction medium should be sufficient for most processes, while it is generally preferred to employ from about 10 to 500 ppm of rhodium and more preferably from 25 to 350 ppm to rhodium.

In addition to the rhodium-organophosphite ligand complex catalyst, free organophosphite ligand (i.e., ligand that is not complexed with the rhodium metal) is also present in the hydroformylation reaction medium. The free organophosphite ligand may correspond to any of the above-defined phosphite ligands discussed above as employable herein. It is preferred that the free organophosphite ligand be the same as the phosphite ligand of the rhodium-organophosphite complex catalyst employed. However, such ligands need not be the same in any given process. The hydroformylation process of this invention may involve up to 100 moles, or higher, of free organophosphite ligand per mole of rhodium metal in the hydroformylation reaction medium. Preferably the hydroformylation process of this invention is carried out in the presence of from about 1 to about 50 moles of phosphite ligand, and more preferably from about 1 to about 4 moles of phosphite ligand, per mole of rhodium metal present in the reaction medium; said amounts of phosphite ligand being the sum of both the amount of phosphite ligand that is bound (complexed) to the rhodium metal present and the amount of free (non-complexed) phosphite ligand present. Of course, if desired, make-up or additional phosphite ligand can be supplied to the reaction medium of the hydroformylation process at any time and in any suitable manner, e.g. to maintain a predetermined level of free ligand in the reaction medium.

The hydroformylation processes encompassed by this invention are also conducted in the presence of an organic solvent for the rhodium-organophosphite complex catalyst and free organophosphite ligand. Depending on the particular catalyst and reactants employed, suitable organic solvents include, for example, alcohols, alkanes, alkenes, alkynes, ethers, aldehydes, higher boiling aldehyde condensation by-products, ketones, esters, amides, tertiary amines, aromatics and the like. Any suitable solvent which does not unduly adversely interfere with the intended hydroformylation process can be employed and such solvents may include those disclosed heretofore commonly employed in known metal catalyzed hydroformylation processes. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be performed if desired and used accordingly. Illustrative preferred solvents employable in the production of optically active aldehydes include ketones (e.g. acetone and methylethyl ketone), esters (e.g. ethyl acetate), hydrocarbons (e.g. toluene), nitrohydrocarbons (e.g. nitrobenzene) and ethers (e.g. tetrahydrofuran (THF) and glyme). The amount of solvent employed is not critical to the subject invention and need only be that amount sufficient to solubilize the catalyst and free ligand of the hydroformylation reaction mixture to be treated by the process of this invention. In general, the amount of solvent may range from about 5 percent by weight up to about 99 percent by weight or more based on the total weight of the hydroformylation reaction mixture starting material.

Accordingly illustrative non-optically active aldehyde products include e.g., propionaldehyde, n-butyraldehyde, isobutyraldehyde, n-valeraldehyde, 2-methyl 1-butyraldehyde, hexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 3-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehydes products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

The hydroformylation processes may involve a liquid catalyst recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures it is common place to continuously remove a portion of the liquid reaction product medium, containing, e.g., the aldehyde product, the solubilized rhodium-phosphite complex catalyst, free phosphite ligand, and organic solvent, as well as by-products produced in situ by the hydroformylation, e.g., aldehyde condensation by-products etc., and unreacted olefinic starting material, carbon monoxide and hydrogen (syn gas) dissolved in said medium, from the hydroformylation reactor, to a distillation zone, e.g., a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains rhodium-phosphite complex catalyst, solvent, free bisphosphite ligand and usually some undistilled aldehyde product is then recycled back, with or with out further treatment as desired, along with whatever by-product and non-volatilized gaseous reactants that might still also be dissolved in said recycled liquid residue, in any conventional manner desired, to the hydroformylation reactor, such as disclosed e.g., in the above-mentioned patents. Moreover the reactant gases so removed by such distillation from the vaporizer may also be recycled back to the reactor if desired.

The distillation and separation of the desired aldehyde product from the rhodium-organophosphite complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures or below on up to total gas pressure of about 50 psig should be sufficient for most purposes.

In the membrane separation of this invention, an organic solvent-resistant membrane composite is used which allows a substantial portion, e.g. at least 60% of the hydroformylation aldehyde products and organic solvent to pass through, while rejecting at least 90% by weight of the rhodium-organophosphite complex catalyst and free organophosphite ligand. The membrane separation is a pressure-driven process and in general the pressure of the feed stream (i.e., the hydroformylation reaction mixture starting material) may range from a low of about 50 pounds per square inch and to a high of about 1500 pounds per square inch. More preferably the pressure of the feed stream of this invention is from about 100 psi to about 600 psi. The "permeate" is the stream which has passed through the membrane, and compared to the feed stream, the permeate is at a greatly reduced pressure. Typically, the permeate is near atmospheric pressure. The permeate contains a greatly reduced amount of the rhodium-organophosphite complex catalyst and free organophosphite ligand dissolved in the bulk of the aldehyde and organic solvent. Said permeate can be recovered in any conventional manner, e.g. by simply collecting it as a liquid. The "raffinate" stream (also called the "concentrate" or "non-permeate" stream) is the stream that does not pass through the membrane. The raffinate contains the bulk of the rhodium-organophosphite complex catalyst and free organophosphite ligand dissolved in some of the aldehyde and organic solvent. The raffinate stream is typically only slightly lower in pressure than the feed stream and can be recycled back to the hydroformylation reactor for reuse. The permeate stream can be repressurized if it is desired to remove more of the complex catalyst and free ligand and sent to another membrane to undergo separation again.

Moreover, while the successful practice of this invention does not depend and is not predicated on any single explanation as to just exactly how such membrane separation actually occurs, it is believed that the efficacy of such separation and the degree to which the hydroformylation reaction mixture starting material feed will interact with the membrane of the Composite membrane employed will depend in large measure upon the relative solubility parameters of said membrane and the aldehyde product of the starting material feed along with the ratio of molar volume of said organophosphite ligand to said aldehyde product as further defined herein. Accordingly as noted herein the present invention advocates Controlling and correlating the relationship of said solubility parameters and molar volume ratio as a means for predetermining which membrane materials will be likely to provide a suitable effective separation between the rhodium-organophosphite complex catalyst and free organophosphite ligand contained in a given aldehyde containing hydroformylation reaction mixture.

Thus for the purpose of this invention, it should be sufficient to simply point out that the composite membrane suitable for use in this invention can be any composite membrane capable of allowing a substantial portion of the aldehyde product and organic solvent of the hydroformylation reaction mixture starting material to pass through said membrane, while rejecting at least 90 percent by weight of the rhodium-organophosphite complex catalyst and free organophosphite ligand present in said hydroformylation reaction mixture starting material, and wherein said aldehyde product has a solubility parameter in relation to the solubility parameter of the membrane of said composite membrane of at least ±50 $\sqrt{kJ/m^3}$ (preferably at least ±100 $\sqrt{kJ/m^3}$) but not more than ±500 $\sqrt{kJ/m^3}$ (preferably not more than ±400 $\sqrt{kJ/m^3}$), and wherein the ratio of the molar volume of said organophosphite ligand to said aldehyde product is $\geq 1.5$ (preferably $\geq 3.0$).

The solubility parameters of the aldehyde products, solvents and ligands encompassed by this invention may be readily calculated from group contribution theory as developed by (1) L. Constantinou and R. Gani, "New Group Contribution Method for Estimating Properties of Pure Compounds," AIChE J., 40(10),1697 (1994) and (2) L. Constantinou, R. Gani, and J. P. O'Connell, "Estimation of the Acentric Factor and the Liquid Molar Volume at 298 K Through a New Group Contribution Method," Fluid Phase Equilibria, 103(1) 11 (1995).

These methods have been expanded to include heat of vaporization and molar volume contributions for the [>P–] derived from triphenylphosphine data. [Daubret, T. E., Danner, R. P., Sibul, H. M., and Stebbins, C. C., "DIPPR® Data Compilation of Pure Compound Properties", Project 801, Sponsor Release, July, 1995, Design Institute for Physical Property Data, AIChE, New York, N.Y.] Extrapolated values of 91.44 kJ/mol and 0.1353 m³/mol were used to derive group contribution increments for [>P–] of −14.5 kJ/mol (for heat of vaporization) and 0.0124 m³/mol (for liquid molar volume).

The solubility parameter of the membrane of the composite membranes encompassed by this invention may be readily obtained from literature sources and/or determined by methods well know in the art. Illustrated specific solubility parameters of various polymer membranes are given in Table 1.

TABLE 1

| Solubility Parameters of Illustrative Polymer Membranes* | |
|---|---|
| Polymer | Solubility Parameter $\sqrt{kJ/m^3}$ |
| Teflon | 400 |
| Polydimethylsiloxane | 471 |
| Polyethylene | 510 |
| Polyisobutylene | 523 |
| Polybutadiene | 555 |
| Polystyrene | 587 |
| Polymethyl methacrylate | 613 |
| Polyvinyl chloride | 626 |

TABLE 1-continued

| Solubility Parameters of Illustrative Polymer Membranes* | |
|---|---|
| Polymer | Solubility Parameter $\sqrt{kJ/m^3}$ |
| Cellulose diacetate | 704 |
| Polyvinylidene chloride | 787 |
| Polyacrylonitrile | 994 |

*Near 25° C.: From J.M. Prausnitz, Molecular Thermodynamics of Fluid-Phase Equilibria, Prentice-Hall, NJ, 1969, p298.
$\sqrt{kJ/m^3}$ represents the square root of kilo Joules per cubic meter.

Illustrative solubility parameters and molar volumes of various specific aldehydes, organic solvents and organophosphorus ligands are given in Table 2.

TABLE 2

| Solubility Parameters and Molar Volumes for Hydroformylation Reaction Components and Membranes | | |
|---|---|---|
| | Solubility Parameter in $\sqrt{kJ/m^3}$ | Molar Volume in m³/kmol |
| Substance Aldehydes | | |
| propionaldehyde | 617.8 | 0.0747 |
| butyraldehyde | 603.3 | 0.0911 |
| valeraldehyde | 593.0 | 0.1075 |
| 3-pentenal | 594.2 | 0.1016 |
| adipaldehyde | 659.6 | 0.1178 |
| naproxen aldehyde | 759.5 | 0.1947 |
| Solvents | | |
| acetone | 632.7 | 0.0748 |
| benzene | 587.1 | 0.0911 |
| MEK | 615.9 | 0.0912 |
| ethyl acetate | 620.0 | 0.0997 |
| Butyraldehyde Trimer | 639.8 | 0.2235 |
| Valeraldehyde Trimer | 622.5 | 0.2735 |
| Ligands | | |
| triethylphosphite | 396.7 | 0.1723 |
| tributylphosphine | 430.9 | 0.2506 |
| triphenylphosphine | 623.5 | 0.2353 |
| triphenylphosphite | 625.6 | 0.2554 |
| Ligand K* | 665.6 | 0.7724 |
| Ligand D* | 677.8 | 0.7166 |
| Ligand A* | 682.9 | 0.5127 |

*Structural formulas and the names of said ligands are given herein above.

Illustrative solubility parameters of various membranes minus the solubility parameters of various aldehyde are shown in Table 3. Illustrative molar volumes of various ligands divided by the molar volumes of various aldehydes are shown in Table 4.

TABLE 3

Solubility Parameters of Membranes Minus the Solubility Parameter of the Aldehyde All Values are in the Units of $\sqrt{kJ/m^3}$, which is the square root of kilo Joules per cubic meter.

| | Membrane Solubility Parameter | Membrane - Propionaldehyde | Membrane - butyraldehyde | Membrane - valeraldehyde | Membrane - 3-pentenal | Membrane - adipaldehyde | Membrane - Naproxen |
|---|---|---|---|---|---|---|---|
| Teflon | 400 | −218 | −203 | −193 | −194 | −260 | −360 |
| Polydimethyl-siloxane | 471 | −147 | −132 | −122 | −123 | −189 | −289 |
| Polyethylene | 510 | −108 | −93 | −83 | −84 | −150 | −250 |
| Polyisobutylene | 523 | −95 | −80 | −70 | −71 | −137 | −237 |
| Polybutadiene | 555 | −63 | −48 | −38 | −39 | −105 | −205 |
| Polystyrene | 587 | −31 | −16 | −6 | −7 | −73 | −173 |
| Polymethyl methacrylate | 613 | −5 | 10 | 20 | 19 | −47 | −147 |
| Polyvinyl chloride | 626 | 8 | 23 | 33 | 32 | −34 | −134 |
| Cellulose diacetate | 704 | 86 | 101 | 111 | 110 | 44 | −56 |
| Polyvinylidene chloride | 787 | 169 | 184 | 194 | 193 | 127 | 27 |
| Polyacrylonitrile | 994 | 376 | 391 | 401 | 400 | 334 | 234 |

TABLE 4

Molar Volume of Ligand Divided by the Molar Volume of Aldehyde

| Ligand | Ligand/ Propionaldehyde | Ligand/ butyraldehyde | Ligand/ valeraldehyde | Ligand/ 3-pentenal | Ligand/ adipaldehyde | Ligand/ Naproxen Aldehyde |
|---|---|---|---|---|---|---|
| triethylphosphite | 2.31 | 1.89 | 1.60 | 1.70 | 1.46 | 0.88 |
| tributylphosphine | 3.35 | 2.75 | 2.33 | 2.47 | 2.13 | 1.29 |
| triphenylphosphine | 3.15 | 2.58 | 2.19 | 2.32 | 2.00 | 1.21 |
| triphenylphosphite | 3.42 | 2.80 | 2.38 | 2.51 | 2.17 | 1.31 |
| Ligand K | 10.34 | 8.48 | 7.19 | 7.60 | 6.56 | 3.97 |
| Ligand D | 9.59 | 7.87 | 6.67 | 7.05 | 6.08 | 3.68 |
| Ligand A | 6.86 | 5.63 | 4.77 | 5.05 | 4.35 | 2.63 |

Structures of Ligands K, D and A are as defined heretofore.

Illustrative examples of such membranes that may be employed in the practice of this invention include, e.g., cellulose acetate (CA), cellulose triacetate, CA-triacetate blends, cellulose esters-mixed, cellulose nitrate, regenerated cellulose, gelatin, aromatic polyamide, polyimide, polybenzimidazole, polybenzimidiazolone, polyacrylonitrile (PAN), PAN-polyvinyl chloride copolymer, PAN-methallyl sulfonate copolymer, polyarylether sulfones, polydimethyl phenylene oxide, polycarbonate, polyester, polytetrafluoroethylene, polyvinylidene fluoride, polypropylene, polyelectrolyte complexes, polymethyl methacrylate, polydimethylsiloxane, and the like (such as disclosed e.g. in "Membranes" by I. Cabasso in the *Encyclopedia of Polymer Science and Technology*, John Wiley and Sons, New York, 1987).

Moreover the composite membrane of this invention includes any suitable effective membrane as defined herein supported on a porous support. Such support materials help provide the structural design of the composite membrane as opposed to the actual desired separation of the process of this invention which is provided by the particular membrane employed. Such support type materials are well known in the art and include e.g. porous supports fabricated from non-woven and woven cellulosics, polyethylene, polypropylene, nylon, polyacrylnitrile, vinyl chloride homo- and co-polymers, polystyrene, polyesters such as polyethylene terephthalate, polyvinylidene fluoride, polytetrafluoroethylene, polydimethylsiloxane, glass fibers, porous carbon, graphite, inorganic supports based on alumina and/or silica, and such inorganic supports coated with zirconium oxides, and the like. Polyethylene and polypropylene may be preferred support materials. Moreover the composite membranes employable in this invention may be formed into any desired shape or configuration e.g. a hollow fiber or tubular membrane or they may be employed as flat sheets. More preferably such composite membranes may be employed in the form of membrane modules (e.g. spiral wound modules).

Accordingly the support material (substrate layer) of the composite membrane is not narrowly critical and may be any porous polymer support that provides a suitable composite membrane for use in this invention Which is insoluble and stable in the organic solvent and aldehyde product of the hydroformylation reaction mixture starting materials of this invention. Moreover such composite membranes suitable for use in this invention may be prepared by any known method heretofore commonly employed in the art. By way of example, as taught in U.S. Pat. No. 5,265,734, a composite membrane may be derived by subjecting a substrate polymer, e.g. a polymer selected from copolymers and homopolymers of ethylenically unsaturate nitriles, to a sequence of stepwise treatments comprising (1) insolubilized the polymer by crosslinking, (2) coating e.g. with a silicone polymer membrane layer and (3) crosslinking the silicone polymer. Such composite membranes may be further characterized by at least one of the following features (a), (b), (c) and (d) namely:

(a) The particular porous support polymer employed;

(b) Prior to step (2), the crosslinked insolubilize substrate obtained in step (1) may be treated, if desired, with a pore protector in absence of curing agents and catalysts therefor;

(c) The membrane, e.g., silicone coating layer may comprise at least one member selected from the group consisting of silanol-terminated polydimethylsiloxane, other silanol-terminated polysiloxanes, other hydroxy-terminated polysiloxanes, silicones containing alkyl groups, silicones containing aryl groups, and silicones containing both alkyl and aryl groups;

(d) Preferably, the composite membrane swells to an extent of no more than about 10% when immersed in said solvents.

The optional pore protector that may be present in such composite membranes may be any suitable polymer and may be selected from the class of polymers that may serve as the membrane, e.g. it may be a silicone polymer having at least one member selected from the group consisting of silanol-terminated polydimethylsiloxane, other silanol-terminated polysiloxanes, other hydroxy-terminated polysiloxanes, silicones containing alkyl groups, silicones containing aryl groups, and silicones containing both alkyl and aryl groups. The substrate layer may be self-supporting or the substrate layer may be supported on another porous material. The insolubilizing step may comprise at least step (i) of the following steps (i) and (ii), namely: (i) treatment with at least one base selected from organic and inorganic bases; (ii) subsequently to step (i), subjection of said substrate to heat-treatment, preferably at a temperature within the range of about 110°–130° C. In U.S. Pat. No. 5,265,734 the substrate is preferably treated with a pore protector (in absence of a curing agent) and then coated with the membrane, e.g., silicone layer which is then crosslinked. The pore protector (which may be, for example, a hydroxy-terminated polysiloxane) is said to serve the dual purposes of: (1) preventing the pores from collapsing when the support is dried during the curing of the subsequently-applied membrane, e.g., silicone layer and (2) preventing passage of the subsequently-applied membrane, e.g., silicone layer, deeply into the pores and thus also preventing an undue reduction of the flux of the finished membrane. Treatment with the pore protector may be carried out, for example, by dipping the membrane substrate into a dilute solution of the pore protector in a low-boiling inert solvent (e.g. a low boiling alcohol having 1 to 4 carbon atoms, such as methanol, ethanol, propanol or butanol). The final membrane silicone layer and the intermediate pore-protecting silicone layer may have any desired suitable total thickness, e.g., a total thickness in the range of from 500 to 5000 Å and, more preferably, in the range of from 1000 to 2000 Å should be suitable for most purposes.

Thus the more preferred composite membranes employable in this invention are those derived from polydimethylsiloxane membranes, such as those composite polydimethylsiloxane membranes encompassed by U.S. Pat. No. 5,265,734, the entire disclosure of which is incorporated herein by reference thereto.

More particularly the membrane separation process of this invention merely comprises contacting the liquid hydroformylation reaction mixture starting materials with the membrane of the composite membrane in any conventional fashion using any suitable equipment and technique, the preferred result being the rejection of at least 90% by weight of the rhodium-organophosphite complex catalyst and free organophosphite ligand, while permitting a substantial amount of the aldehyde product and organic solvent to pass through the membrane as a permeate. In general merely allowing the liquid hydroformylation reaction mixture starting material to pass over the surface of the membrane of the composite membrane at a predetermined pressure and flow rate should be sufficient to accomplish the desired result.

As noted above the contact of the hydroformylation reaction mixture starting material and the membrane may be carried out at a pressure ranging from about 50 psi to about 1500 psi. For instance nanofiltration is generally carried out at a pressure of from about 75 psi to 600 psi; ultrafiltration is generally carried out at a pressure of from about 25 psi to 200 psi; while reverse osmosis is generally carried out at a pressure of from about 250 psi to 1000 psi. Preferably the contact of the hydroformylation reaction mixture starting materials and membranes in this invention is generally conducted at a pressure of about 100 psi to 600 psi.

In general the flow rate of the hydroformylation reaction mixture starting materials over the membrane in this invention may be from about 2 gal/ft$^2$.hr to about 800 gal/ft$^2$.hr, with preferred commercial-type flow rates being from about 3 gal/ft$^2$.hr to 125 gal/ft$^2$.hr As a practical matter however any suitable flow rate that helps achieve the end result desired may be employed.

The temperature at which the contact of the hydroformylation reaction mixture starting material and membrane takes place is also not narrowly critical. Broadly, said contact may be carried out at any suitable temperature, e.g. from about −20° C. to about 120° C. As a practical matter, the temperature employed is preferably from about 0° C. to about 60° C.

Accordingly it is considered that the membrane separation of the process of this invention may possibly allow one to eliminate the need for conventional distillation and/or vaporization separation of the desired aldehyde product from the rhodium-organophosphite complex catalysts contained in the hydroformylation reaction product mixtures of conventional liquid catalyst recycle hydroformylations. Alternatively the membrane separation process of this invention may also serve as a means for treating, all or any part of any conventional liquid catalyst residue hydroformylation recycle stream obtained, after first conventionally separating the desired aldehyde product from the rhodium-organophosphite complex catalyst contained in the hydroformylation reaction product mixtures by distillation and/or vaporization, in order to remove the aldehyde trainers and tetramers from said catalyst recycle streams. Such a procedure may serve to help control the concentration of such aldehyde trimer and tetramer in situ type by-products in the hydroformylation reactor and thus prevent any adverse build-up of same in the reactor.

Of course it is to be understood that while the optimization of the subject invention necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

The optically active aldehyde products and derivatives of said products have a wide range of utility that is well known and documented in the art, e.g. they may especially be useful as pharmaceuticals, flavors, fragrances, agricultural chemicals and the like. Illustrative therapeutic applications, include, for example, non-steroidal anti-inflammatory drugs, ACE inhibitors, beta-blockers, analgesics, bronchodilators, spasmolytics, antihistimines, antibiotics, antitumor agents and the like.

Finally, the non-optically active aldehyde products of the hydroformylation process of this invention have a wide range of utility that is well known and documented in the prior art e.g. they are especially useful as starting materials for the production of alcohols and acids.

The following examples are illustrative of the present invention and are not to be regarded as limitative. It is to be understood that all of the parts, percentages and proportions referred to herein and in the appended claims are by weight unless otherwise indicated.

EXAMPLE 1

A crude hydroformylation reaction mixture was processed through a membrane to remove the rhodium and ligand. Said reaction mixture was obtained by hydroformylating a solubilized organic solution of 6-methoxy-2-vinylnaphthalene (about 395 g), Ligand K [(2R, 4R)-Di[2,2'-(3,3'-di-tert-butyl-5,5'-dimethoxy-1,1'-biphenyl)]-2,4-pentyl diphosphite] (about 6 g), $Rh_4(CO)_{12}$ (about 0.9 g) and acetone (about 1500 mL) at about 250 psi with 1:1 $H_2/CO$. Said hydroformylation reaction mixture was found to contain 2-(6-methoxy-2-naphthyl)propionaldehyde, (naproxen aldehyde, about 30 wt %) dissolved in acetone (about 70 wt %). The crude reaction mixture also contained rhodium (about 263 ppm) and about 0.2 weight percent of said Ligand K (about 50% complexed and 50% free).

Three composite membranes were arranged in parallel and used as follows: Three 2 inch circles were cut from an 8 inch×11 inch sheet of MPF-50 (Lot #021192, code 5107) a polydimethylsiloxane composite membrane obtained from Membrane Products Kiryat Weizmann Ltd. and which is believed to be within the scope of U.S. Pat. No. 5,265,734. These circles were placed into three Osmonics membrane holders. The crude hydroformylation mixture (feed) was placed into a 2L Hoke cylinder under nitrogen. The feed was pumped to 500 psi at a flow rate of about 380 mL/min. The feed flowed through a 60 micron filter and then was split into three streams which went to the membranes. Flowmeters were used to ensure that the flow was split equally to the holders. The permeates were combined and collected under nitrogen. The raffinates flowed to a back pressure regulator and were then returned to the Hoke cylinder.

The solubility parameter of the 2-(6-methoxy-2-naphthyl) propionaldehyde product is 760 $\sqrt{kJ/m^3}$, while the solubility parameter for the polydimethylsiloxane membrane is 471 $\sqrt{kJ/m^3}$, the difference between said solubilities being −289 $\sqrt{kJ/m^3}$. The molar volume for the 2-(6-methoxy-2-naphthyl)propionaldehyde product is 0.1947 $m^3/kmol$ and the molar volume for Ligand K is 0.7724 $m^3/kmol$, the ratio of said ligand to said aldehyde being 3.97.

About 1500 g of the crude hydroformylation reaction mixture was permeated and the rhodium content of the resulting permeate was about 69.4 ppm. Such a high mount of rhodium in the permeate indicated a rejection of only about 74% by weight of the catalyst and ligand.

It was subsequently determined that the membrane cells, more specifically the O-rings that hold the membrane composites in place, were not set properly, and that this allowed the liquid reaction mixture to path around the membrane instead of through the membrane. it is believed that such was the cause of the apparent low rejection of catalyst and ligand.

EXAMPLE 2

The hydroformylation reaction and membrane separation procedures of Example 1 were repeated.

The same three composite membrane set up was employed, with care being taken this time to insure that the membrane composites were properly set in the O-rings of the membrane holders. The three composite membranes were arranged in parallel and used as in Example 1. Three 2 inch circles were cut from an 8 inch×11 inch sheet of MPF-50 polydimethylsiloxane composite membrane obtained from Membrane Products Kiryat Weizmann Ltd. These circles were placed into three Osmonics membrane holders. The crude hydroformylation mixture (feed) was placed into a 2 L Hoke cylinder under nitrogen. The feed was pumped to 500 psi at a flow rate of about 380 mL/min. The feed flowed through a 60 micron filter and then was split into three streams which went to the membranes. Flowmeters were used to ensure that the flow was split equally to the holders. The permeates were combined and collected under nitrogen. The raffinate flowed to a back pressure regulator and were then returned to the Hoke cylinder.

The solubility parameter of the 2-(6-methoxy-2-naphthyl) propionaldehyde product is 760 $\sqrt{kJ/m^3}$, while the solubility parameter for the polydimethylsiloxane membrane is 471 $\sqrt{kJ/m^3}$, the difference between said solubilities being −289 $\sqrt{kJ/m^3}$. The molar volume for the 2-(6-methoxy-2-naphthyl)propionaldehyde product is 0.1947 $m^3/kmol$ and the molar volume for said Ligand K [2R, 4R)-Di[2,2'-(3,3'-di-tert-butyl-5,5'-dimethoxy-1,1'-biphenyl)]-2,4-pentyl diphosphite] is 0.7724 $m^3/kmol$, the ratio of said ligand to said aldehyde being 3.97.

The membrane separation feed was a 4 L batch of the crude hydroformylation reaction mixture which contained 2-(6-methoxy-2-naphthyl)-propionaldehyde (about 30 wt %) in acetone (about 70 wt %). The mixture also contained rhodium (about 389 ppm) and said Ligand K. About 3325 g of this feed solution was permeated through the composite membranes and the resulting permeate solution had a rhodium content of about 36.3 ppm. Samples of the feed solution and of the permeate were acquired at the same time and the feed was found to have about 389 ppm rhodium, while the permeate was found to have about 21.6 ppm rhodium, which is a rejection of about 94.5% by weight of the catalyst and ligand. The system was emptied, cleaned with acetone and the waste discarded.

The 3325 g of the permeate solution containing 36.3 ppm rhodium was placed back into the Hoke cylinder and about 1439 g of this solution was again permeated through the composite membranes. This second resulting permeate solution contained about 5.6 ppm rhodium. Samples of the feed and of the permeate were acquired at the same time and the feed was found to have 51.1 ppm rhodium, while the permeate was found to have 3.8 ppm rhodium, which is a rejection of about 92.6% by weight of the catalyst and ligand.

The 1439 g of the solution containing 5.6 ppm rhodium was placed back into the Hoke cylinder and passed back through the composite membranes for the third time. About 935 g of this solution was permeated through the membranes and the resulting permeate had about 1.2 ppm rhodium. Samples of the feed and of the permeate were acquired at the same time and the feed was found to have 18.2 ppm rhodium, while the permeate was found to have 1.3 ppm rhodium which is a rejection of 92.9% by weight of the catalyst and ligand.

EXAMPLE 3

Using the same set-up, equipment and composite membranes as described in Example 2, organic solubilized solutions of C5 and C6 aldehydes were passed over the membranes to separate the catalyst and ligands from such solutions.

(a) A mixture of 90 wt % butyraldehyde, 10 wt % trimer of butyraldehyde with 27 ppm rhodium and 0.14 wt % of Ligand D 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin] was passed over said MPF-50 composite membranes. The butyraldehyde has a solubility parameter of 603 $\sqrt{kJ/m^3}$, while the polydimethylsiloxane membrane has a solubility parameter of 471 $\sqrt{kJ/m^3}$, the difference between said solubilities being −132 $\sqrt{kJ/m^3}$. The molar volume of butyraldehyde is 0.0911 $m^3/kmol$ and the molar volume for Ligand D is 0.7166 $m^3/kmol$, the ratio of said ligand to said aldehyde being 7.87. The permeate solution was collected at a rate of 6 gallons per square foot of membrane per day and contained less than 0.8 ppm rhodium (greater than 97% rejection) and 0.0056 wt % Ligand D (a rejection of 96%).

(b) A mixture of 90 wt % valeraldehyde, 10 wt % trimer of butyraldehyde with 60 ppm rhodium and 0.27 wt % of Ligand D 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin] was passed over said MPF-50 composite membranes. The valeraldehyde has a solubility parameter of 593 $\sqrt{kJ/m^3}$, while the polydimethylsiloxane membrane has a solubility parameter of 471 $\sqrt{kJ/m^3}$, the difference between said solubilities being −122 $\sqrt{kJ/m^3}$. The molar volume of valeraldehyde is 0.108 $m^3/kmol$ and the molar volume for Ligand D is 0.7166 $m^3/kmol$, the ratio of said ligand to said aldehyde being 6.67. The permeate solution was collected at a rate of 7 gallons per square foot of membrane per day and contained less than 0.9 ppm rhodium (greater than 98.5% rejection) and 0.0081 wt % Ligand D (a rejection of 97%).

(c) The same experiment performed in run (b) above was repeated with another polydimethylsiloxane composite membrane, i.e. MPF-60, obtained from Membrane Products Kiryat Weizmann Ltd. and a mixture of 90 wt % valeraldehyde, 10 wt % trimer of valeraldehyde with 500 ppm rhodium and 1.25 wt % of Ligand D. The permeate was collected at a rate of 0.5 gallons per square foot of membrane per day and contained 4.2 ppm rhodium (a 99.15% rejection) and non-detectable amounts of Ligand D (near 100% rejection).

EXAMPLE 4

In this example a spiral wound packaged polydimethylsiloxane MPS-50 composite membrane obtained from Membrane Products Kiryat Weizmann, Ltd. was used. This membrane module contained 2.7 $ft^2$ of membrane, and so it represents a small commercial type unit.

A crude hydroformylation reaction mixture similar to the crude reaction product produced in Example 1 above was processed through a membrane to remove the rhodium and ligand. The crude reaction mixture, to which acetone was added, contained 2-(6-methoxy-2-naphthyl) propionaldehyde (12 wt %) dissolved in acetone (88 wt %) and also rhodium (90 ppm) and said Ligand K [2R, 4R)-Di [2,2'-(3,3'-di-tert-butyl-5,5'-dimethoxy-1,1'-biphenyl)]-2,4-pentyl diphosphite].

The solubility parameter of 2-(6-methoxy-2-naphthyl) propionaldehyde is 760 ($\sqrt{kJ/m^3}$, while the solubility parameter for the polydimethylsiloxane membrane is 471 $\sqrt{kJ/m^3}$, the difference between said solubilities being −289 $\sqrt{kJ/m^3}$. The molar volume of the 2-(6-methoxy-2-naphthyl) propionaldehyde is 0.1947 $m^3/kmol$ and the molar volume for Ligand K is 0.7724 $m^3/kmol$, with the molar volume ratio of said aldehyde to said Ligand K being 3.97.

Two gallons of the crude hydroformylation reaction mixture feed was added to a Hoke vessel (and associated tubing), which is used as the feed tank. The solution was pumped at 1 gallon per minute through a 10 micron filter and associated valves and flowmeters to the MPS-50 composite membrane. The bulk of the aldehyde solution flowed through the MPS-50 membrane module, which is contained in a pressure shell, and the raffinate flowed to a back pressure regulator which was set for 400 psig. The raffinate then flowed through heat exchanger, for temperature control, and back to the feed tank. The permeate, flowed back to the feed tank. Sampling valves allowed samples to be acquired for analyses.

When the temperature of the module was set at 22° C., the rejection of the rhodium catalyst was found to be 92.8%, at a permeate flow rate of about 39 gallons of permeate per square foot of membrane per day. When the module temperature was set at 18° C., the rejection of the rhodium catalyst was measured to be 93.6% at the same permeate flow rate.

EXAMPLE 5

A crude hydroformylation reaction mixture similar to the crude reaction product produced in Example 1 above was processed through a membrane to remove the rhodium and ligand. The crude reaction product contained 2-(6-methoxy-2-naphthyl)propionaldehyde (25 wt %) dissolved in acetone (75 wt %) and also contained rhodium (300 ppm) and said Ligand K [2R, 4R)-Di[2,2'-(3,3'-di-tert-butyl-5,5'-dimethoxy-1,1'-biphenyl)]-2,4-pentyl diphosphite]. A similar membrane apparatus was used as outlined in Example 1, except only one composite membrane module was employed and which is similar in design to the Osmonics cell design used in Example 1.

The solubility parameter of 2-(6-methoxy-2-naphthyl) propionaldehyde, is 760 ($\sqrt{kJ/m^3}$, while the solubility parameter for the polydimethylsiloxane membrane is 471 $\sqrt{kJ/m^3}$, with the difference between said solubilities being −289 $\sqrt{kJ/m^3}$. The molar volume of the 2-(6-methoxy-2-naphthyl)propionaldehyde is 0.1947 $m^3/kmol$ and the molar volume for Ligand K is 0.7724 $m^3/kmol$, with the molar volume ratio of said aldehyde to said Ligand K being 3.97.

The crude reaction product was split into three batches. One was not touched. The acetone was stripped out of the other two batches, and to one methyl ethyl ketone was added, and to the other ethyl acetate was added. Thus three identical batches of the rhodium-Ligand K complex catalyst in said product aldehyde, the 2-(6-methoxy-2-naphthyl) propionaldehyde, were prepared save for the three different solvents employed.

A series of membrane separations were then conducted one after the other using said three different solubilized aldehyde product solutions. After each run the system was emptied and cleaned so as to prepare for a following trial run.

The first trial run employed the ethyl acetate-based solubilized aldehyde product solution and yielded an 87% by weight rejection of the rhodium catalyst.

The second trial run employed the acetone-based solubilized aldehyde product solution and yielded an 98% by weight rejection of the rhodium catalyst.

The third trial run employed the methyl ethyl ketone-based solubilized aldehyde product solution and yielded an 98.3% by weight rejection of the rhodium catalyst.

The fourth trail run was a rerun of the ethyl acetate-based solubilized aldehyde product solution and yielded a 97.8% by weight rejection of rhodium catalyst The fifth trial run was rerun of the acetone-based solubilized aldehyde product solution and yielded a 99.4% by weight rejection of rhodium catalyst.

The sixth trial run was a rerun of methyl ethyl ketone-based solubilized aldehyde product solution and yielded a 98% by weight rejection of rhodium catalyst.

EXAMPLE 6

The acetone-based solubilized aldehyde product mixture of Example 5 was passed over a polydimethylsiloxane membrane supported on a polyamidimid support which may be obtained from GKSS-Forschungszentrum Geesthacht GmbH (Germany) under the designation Torlon using a similar composite membrane set-up as described in Example 5. A 94.7% by weight rejection of the rhodium catalyst from the aldehyde product mixture feed was obtained.

Although the invention has been illustrated by certain of the preceding examples, it is not to be construed as being limited thereby; but rather, the invention encompasses the generic area as herein before disclosed. Various modifications and variations of this invention will be obvious to a worker skilled in the art and it is to be understood that such modifications and variations are to be included within the purview of this application and the spirit and scope of the appended claims.

What is claimed is:

1. A process for separating an organic solubilized rhodium-organophosphite complex catalyst and free organophosphite ligand from a non-aqueous hydroformylation reaction mixture, said mixture containing, in addition to said catalyst and free ligand, aldehyde product and an organic solvent, which comprises, (i) contacting said non-aqueous hydroformylation reaction mixture with a composite membrane at a pressure from about 50 psi to about 1500 psi so as to allow a substantial portion of said aldehyde product and organic solvent to pass through said membrane, while rejecting at least 90 percent by weight of said catalyst and free ligand; wherein said aldehyde product has a solubility parameter in relation to the solubility parameter of the membrane of said composite membrane of at least ±50 $\sqrt{kJ/m^3}$ units, but not more than ±500 $\sqrt{kJ/m^3}$ units, and wherein the ratio of the molar volume of said organophosphite ligand to said aldehyde product is $\geq 1.5$; and (ii) recovering said aldehyde product and organic solvent as a permeate.

2. A process as defined in claim 1, wherein the aldehyde product is an optically active aldehyde.

3. A process as defined in claim 2, wherein said organophosphite is a organobisphosphite.

4. A process as defined in claim 2, wherein the membrane of said composite membrane is a polydimethylsiloxane polymer.

5. A process as defined in claim 1, wherein the aldehyde product is a non-optically active aldehyde.

6. A process as defined in claim 5, wherein said organophosphite is an organobisphosphite.

7. A process as defined in claim 5, wherein the membrane of said composite membrane is a polydimethylsiloxane polymer.

8. A process as defined in claim 1, wherein the aldehyde product has a solubility parameter in relation to the solubility parameter of the membrane of the composite membrane of at least ±100 $\sqrt{kJ/m^3}$ units but not more than ±400 $\sqrt{kJ/m^3}$ units.

9. A process as defined in claim 8, wherein the ratio of the molar volume of said organophosphite ligand to said aldehyde product is $\geq 3.0$.

10. A process as defined in claim 9, wherein said organophosphite is a organobisphosphite, wherein the membrane of said composite membrane is a polydimethylsiloxane polymer and wherein said aldehyde product is an optically-active aldehyde.

11. A process as defined in claim 9, wherein said organophosphite is a organobisphosphite, wherein the membrane of said composite membrane is a polydimethylsiloxane polymer and wherein said aldehyde product is an non-optically-active aldehyde.

* * * * *